(12) United States Patent
Soula et al.

(10) Patent No.: US 7,709,445 B2
(45) Date of Patent: May 4, 2010

(54) COLLOIDAL SUSPENSION OF NANOPARTICLES BASED ON AN AMPHIPHILIC COPOLYMER

(75) Inventors: Gérard Soula, Meyzieu (FR); Nathan Bryson, Millery (FR)

(73) Assignee: Flamel Technologies, Venissieuz (FR)

( * ) Notice: Subject to any disclaimer, the term of this patent is extended or adjusted under 35 U.S.C. 154(b) by 0 days.

(21) Appl. No.: 10/473,821

(22) PCT Filed: Mar. 26, 2002

(86) PCT No.: PCT/FR02/01045

§ 371 (c)(1),
(2), (4) Date: Feb. 20, 2004

(87) PCT Pub. No.: WO02/078677

PCT Pub. Date: Oct. 10, 2002

(65) Prior Publication Data

US 2004/0138095 A1 Jul. 15, 2004

(30) Foreign Application Priority Data

Apr. 2, 2001 (FR) .................................. 01 04512

(51) Int. Cl.
*A61K 38/02* (2006.01)
*A61K 9/10* (2006.01)
(52) U.S. Cl. .................. 514/12; 514/2; 514/937; 514/941; 530/345; 424/400; 516/8.1
(58) Field of Classification Search .................. 514/12, 514/937, 941; 530/345; 516/8.1
See application file for complete search history.

(56) References Cited

U.S. PATENT DOCUMENTS

| | | | |
|---|---|---|---|
| 2,680,749 A | 6/1954 | Cawley et al. |
| 3,536,672 A | 10/1970 | Fujimoto et al. |
| 4,126,628 A | 11/1978 | Paquet |
| 4,321,253 A | 3/1982 | Beatty |
| 4,351,337 A | 9/1982 | Sidman |
| 4,443,549 A | 4/1984 | Sadowski |
| 4,450,150 A | 5/1984 | Sidman |
| 4,615,697 A | 10/1986 | Robinson |
| 4,652,441 A | 3/1987 | Okada et al. |
| 4,661,345 A | 4/1987 | Tuomanen |
| 4,748,023 A | 5/1988 | Tamas et al. |
| 4,766,106 A | 8/1988 | Katre et al. |
| 4,835,293 A | 5/1989 | Bhatia |
| 4,888,398 A | 12/1989 | Bichon et al. |
| 4,892,733 A | 1/1990 | Bichon et al. |
| 4,894,240 A | 1/1990 | Geoghegan et al. |
| 4,904,479 A | 2/1990 | Illum |
| 4,976,968 A | 12/1990 | Steiner |
| 5,023,349 A | 6/1991 | Bhatia |
| 5,084,278 A | 1/1992 | Mehta et al. |
| 5,102,872 A | 4/1992 | Singh et al. |
| 5,204,108 A | 4/1993 | Illum |
| 5,286,495 A | 2/1994 | Batich et al. |
| 5,286,497 A | 2/1994 | Hendrickson et al. |
| 5,399,331 A | 3/1995 | Loughrey et al. |
| 5,449,513 A | 9/1995 | Yokoyama et al. |
| 5,510,103 A | 4/1996 | Yokoyama et al. |
| 5,514,380 A | 5/1996 | Song et al. |
| 5,589,455 A * | 12/1996 | Woo ........................... 514/11 |
| 5,609,872 A | 3/1997 | Ahlborg et al. |
| 5,656,722 A | 8/1997 | Dorschug et al. |
| 5,780,579 A | 7/1998 | Soula et al. |
| 5,834,422 A | 11/1998 | Balschmidt et al. |
| 5,852,109 A | 12/1998 | Makino et al. |
| 5,863,900 A | 1/1999 | Russell-Jones |
| 5,869,703 A | 2/1999 | Kim et al. |
| 5,872,210 A | 2/1999 | Medabalimi |
| 5,876,969 A | 3/1999 | Fleer et al. |
| 5,904,936 A | 5/1999 | Huille et al. |
| 5,981,761 A | 11/1999 | Chou et al. |
| 6,143,314 A | 11/2000 | Chandrashekar et al. |
| 6,153,193 A | 11/2000 | Kabanov et al. |
| 6,180,141 B1 | 1/2001 | Lemercier et al. |
| 6,193,953 B1 * | 2/2001 | Lohrmann et al. ......... 424/9.52 |

(Continued)

FOREIGN PATENT DOCUMENTS

CA        2068366        11/1992

(Continued)

OTHER PUBLICATIONS

Harada, Macromolecules 29, 6183-88, 1996.*

(Continued)

*Primary Examiner*—David Lukton
(74) *Attorney, Agent, or Firm*—Patton Boggs LLP (57) ABSTRACT

An aqueous suspension, stable in physiological medium, of nanoparticles for delivering active principles such as insulin. The delivery particles are based on a three-block copolymer: polyethylene glycol/hydrophilic polyaminoacid/hydrophobic polyaminoacid. These three-block copolymers can be associated with an active principle without denaturing it, and perform a controlled and long-term release of the active principle in vivo, and thus provide the active principle with a very prolonged release. Also disclosed is a powder form solid from which are derived the delivery particles, the preparation of the powder-form solid, a suspension of delivery particles based on the three-block copolymer, and pharmaceutical specialties obtainable from the delivery particles filled with active principle.

12 Claims, 3 Drawing Sheets

U.S. PATENT DOCUMENTS

| | | | |
|---|---|---|---|
| 6,197,535 B1 | 3/2001 | Bandyopadhyay et al. | |
| 6,201,072 B1 | 3/2001 | Rathi et al. | |
| 6,235,282 B1 | 5/2001 | Riviere et al. | |
| 6,284,267 B1 | 9/2001 | Aneja | |
| 6,309,633 B1 * | 10/2001 | Ekwuribe et al. | 424/85.1 |
| 6,313,095 B1 | 11/2001 | Adams et al. | |
| 6,313,260 B2 | 11/2001 | Gruning et al. | |
| 6,320,017 B1 | 11/2001 | Ansell | |
| 6,500,448 B1 | 12/2002 | Johnson et al. | |
| 6,576,254 B1 | 6/2003 | Uchegbu | |
| 6,630,171 B1 | 10/2003 | Huille et al. | |
| 6,933,269 B2 | 8/2005 | Jordan et al. | |
| 6,946,146 B2 | 9/2005 | Mulye | |
| 7,030,155 B2 | 4/2006 | Lambert et al. | |
| 7,226,618 B1 | 6/2007 | Touraud et al. | |
| 7,261,875 B2 | 8/2007 | Li et al. | |
| 7,270,832 B2 | 9/2007 | Bryson et al. | |
| 2001/0000510 A1 | 4/2001 | Sakurai et al. | |
| 2002/0068085 A1 | 6/2002 | Rudnic et al. | |
| 2003/0133980 A1 | 7/2003 | Costantino et al. | |
| 2004/0038885 A1 | 2/2004 | Bryson et al. | |
| 2004/0063628 A1 | 4/2004 | Piccariello et al. | |
| 2004/0071716 A1 | 4/2004 | Jansen et al. | |
| 2004/0175424 A1 | 9/2004 | Castan et al. | |
| 2005/0158392 A1 | 7/2005 | Kim et al. | |
| 2006/0099264 A1 | 5/2006 | Chan et al. | |
| 2007/0010652 A1 | 1/2007 | Angot et al. | |
| 2007/0160568 A1 | 7/2007 | Angot et al. | |
| 2007/0178126 A1 | 8/2007 | Angot et al. | |
| 2007/0190162 A1 | 8/2007 | Caillot et al. | |
| 2007/0196497 A1 | 8/2007 | Pouliquen et al. | |
| 2007/0248686 A1 | 10/2007 | Touraud et al. | |
| 2007/0254828 A1 | 11/2007 | Dubreucq et al. | |
| 2007/0265192 A1 | 11/2007 | Soula et al. | |
| 2008/0014250 A1 | 1/2008 | Soula et al. | |
| 2008/0015332 A1 | 1/2008 | Bryson et al. | |
| 2009/0012028 A1 | 1/2009 | Chan et al. | |
| 2009/0110742 A1 | 4/2009 | Constancis et al. | |

FOREIGN PATENT DOCUMENTS

| | | |
|---|---|---|
| EP | 0 198 769 | 10/1986 |
| EP | 0 179 023 | 1/1991 |
| EP | 0583955 | 2/1994 |
| EP | 0 601 508 | 6/1994 |
| EP | 0 721 776 | 7/1996 |
| EP | 0 734 720 | 10/1996 |
| EP | 0 963 758 | 12/1999 |
| FR | 2 732 218 | 10/1996 |
| FR | 2 746 035 | 9/1997 |
| FR | 2 838 964 | 10/2003 |
| FR | 2 840 614 | 12/2003 |
| FR | 2 843 117 | 2/2004 |
| FR | 2 855 521 | 12/2004 |
| FR | 2 860 516 | 4/2005 |
| FR | 2 873 040 | 1/2006 |
| FR | 2 881 140 | 7/2006 |
| FR | 2 915 748 | 11/2008 |
| GB | 966 760 | 8/1964 |
| GB | 1 024 393 | 3/1966 |
| GB | 1 202 765 | 8/1970 |
| GB | 2 041 517 | 9/1980 |
| GB | 2 240 547 | 8/1991 |
| WO | WO 85/02092 | 5/1985 |
| WO | WO 87/02219 | 4/1987 |
| WO | WO 87/03891 | 7/1987 |
| WO | WO 88/01213 | 2/1988 |
| WO | WO 88/07078 | 9/1988 |
| WO | WO 89/08449 | 9/1989 |
| WO | WO 91/06286 | 5/1991 |
| WO | WO 91/06287 | 5/1991 |
| WO | WO 96/40279 | 12/1996 |
| WO | WO 97/02810 | 1/1997 |
| WO | WO 97/34584 | 9/1997 |
| WO | WO 98/11874 | 3/1998 |
| WO | WO 99/18142 | 4/1999 |
| WO | WO 99/61512 | 12/1999 |
| WO | WO 00/18821 | 4/2000 |
| WO | WO 00/30618 | 6/2000 |
| WO | WO 00/71163 | 11/2000 |
| WO | WO 00/78791 | 12/2000 |
| WO | WO 01/37809 | 5/2001 |
| WO | WO 02/28521 | 4/2002 |
| WO | WO 02/39984 | 5/2002 |
| WO | WO 02/098951 | 12/2002 |
| WO | WO 02/098952 | 12/2002 |
| WO | WO 03/002096 | 1/2003 |
| WO | WO 03/013467 | 2/2003 |
| WO | WO 03/104303 | 12/2003 |
| WO | WO 2004/013206 | 2/2004 |
| WO | WO 2004/060968 | 7/2004 |
| WO | WO 2004/108796 | 12/2004 |
| WO | WO 2005/033181 | 4/2005 |
| WO | WO 2005/051416 | 6/2005 |
| WO | WO 2006/016078 | 2/2006 |
| WO | WO 2007/034320 | 3/2007 |
| WO | WO 2007/016143 | 10/2007 |

OTHER PUBLICATIONS

Yokoyama et al., "Incorporation of Water-insoluble Anticancer Drug into Polymeric Micelles and Control of Their Particle Size," 55 *J. Controlled Release* 219 (1998).

Fuller et al., "A Procedure for the Facile Synthesis of Amino-Acid N-Carboxyanhydrides," *Biopolymers*, 1976, vol. 15, pp. 1869-1871.

H.R. Kricheldorf, "-Amino Acid N-Carboxy Anydride and Related Heterocycles," *Springer-Verlag, Berlin Heidelberg* 1987.

M. J. Humphrey, "The Oral Bioavailability of Peptides and Related Drugs," *Delivery System for Peptide Drugs*, Plenum Press, 1986, pp. 139-151.

In the U.S. Patent and Trademark Office, Final Office Action in re: U.S. Appl. No. 09/856,378, dated Jan. 28, 2003, 11 pages.

In the U.S. Patent and Trademark Office, Final Office Action in re: U.S. Appl. No. 09/856,378, dated Sep. 27, 2002, 7 pages.

In the U.S. Patent and Trademark Office, Final Office Action in re: U.S. Appl. No. 10/130,783, dated Jan. 27, 2006, 19 pages.

In the U.S. Patent and Trademark Office, Final Office Action in re: U.S. Appl. No. 10/398,133, dated Mar. 24, 2009, 8 pages.

In the U.S. Patent and Trademark Office, Non-Final Office Action in re: U.S. Appl. No. 10/398,133, dated Jun. 13, 2008, 13 pages.

In the U.S. Patent and Trademark Office, Non-Final Office Action in re: U.S. Appl. No. 10/398,133, dated Nov. 4, 2005, 10 pages.

In the U.S. Patent and Trademark Office, Non-Final Office Action in re: U.S. Appl. No. 10/398,133, dated Sep. 28, 2007, 15 pages.

In the U.S. Patent and Trademark Office, Non-Final Office Action in re: U.S. Appl. No. 10/398,134, dated Oct. 17, 2006, 14 pages.

In the U.S. Patent and Trademark Office, Non-Final Office Action in re: U.S. Appl. No. 10/398,134, dated May 12, 2005, 11 pages.

In the U.S. Patent and Trademark Office, Non-Final Office Action in re: U.S. Appl. No. 10/473,821, dated Mar. 24, 2008, 9 pages.

In the U.S. Patent and Trademark Office, Non-Final Office Action in re: U.S. Appl. No. 10/473,821, dated May 2, 2006, 8 pages.

In the U.S. Patent and Trademark Office, Final Office Action in re: U.S. Appl. No. 10/516,733, dated Jun. 17, 2008, 9 pages.

In the U.S. Patent and Trademark Office, Non-Final Office Action in re: U.S. Appl. No. 10/516,733, dated Feb. 26, 2009, 4 pages.

In the U.S. Patent and Trademark Office, Non-Final Office Action in re: U.S. Appl. No. 10/516,733, dated Feb. 5, 2007, 7 pages.

In the U.S. Patent and Trademark Office, Non-Final Office Action in re: U.S. Appl. No. 10/516,733, dated Sep. 12, 2007, 7 pages.

In the U.S. Patent and Trademark Office, Final Office Action in re: U.S. Appl. No. 10/558,617, dated Jun. 26, 2009, 14 pages.

In the U.S. Patent and Trademark Office, Final Office Action in re: U.S. Appl. No. 10/558,617, dated Jan. 30, 2008, 8 pages.

In the U.S. Patent and Trademark Office, Non-Final Office Action in re: U.S. Appl. No. 10/558,617, dated Dec. 22, 2008, 8 pages.
In the U.S. Patent and Trademark Office, Non-Final Office Action in re: U.S. Appl. No. 10/558,617, dated Jun. 29, 2007, 10 pages.
In the U.S. Patent and Trademark Office, Non-Final Office Action in re: U.S. Appl. No. 10/580,035, dated Dec. 3, 2008, 25 pages.
In the U.S. Patent and Trademark Office, Non-Final Office Action in re: U.S. Appl. No. 11/601,691, dated Apr. 3, 2009, 29 pages.
In the U.S. Patent and Trademark Office, Non-Final Office Action in re: U.S. Appl. No. 11/878,947, dated Jul. 20, 2009, 11 pages.
In the U.S. Patent and Trademark Office, Final Office Action in re: U.S. Appl. No. 10/574,475, dated Nov. 7, 2008, 4 pages.
In the U.S. Patent and Trademark Office, Final Office Action in re: U.S. Appl. No. 10/574,475, dated Jan. 31, 2008, 8 pages.
In the U.S. Patent and Trademark Office, Non-Final Office Action in re: U.S. Appl. No. 11/509,783, dated Jan. 31, 2008, 9 pages.
Akiyoshi et al., "Self-Assembled Hydrogel Nanoparticle of Cholesterol-Bearing Pullulan as a Carrier of Protein Drugs: Complexation and Stabilization of Insulin," *J. Control. Release*, 1998; 54(3): 313-320.
Akiyoshi et al., "Stabilization of Insulin upon Supramolecular Complexation with Hydrophobized Polysaccharide Nanoparticle," Chemistry Letters, 1995; 8:707-708.
Candau, S., Chapter 3: Light Scattering, *Surfactant Solutions*, vol. 22, Ed. R. Zana, M. Dekker, Inc., NY (1987) p. 147-207.
Database WPI Week 200274, AN 2002-685440, Derwent Publications Ltd., London, GB, 2007.
Database WPI Week 200355, AN 2002-694010, Derwent Publications Ltd., London, GB, 2007.
Database WPI Week 200644, AN 2002-260230, Derwent Publications Ltd., London, GB, 2008.
Davies, J.T., "A Quantitative Kinetic Theory of Emulsion Type, I. Physical Chemistry of the Emulsifying Agent," *Proceedings of the Second International Congress of Surface Activity*, 1957; pp. 426-439.
Forssen et al., "Improved Therapeutic Benefits of Doxorubicin by Entrapment in Anionic Liposomes," Cancer Res., 1983; 43:546-550.
Gao et al., "Measurement of the Binding of Proteins to Polyelectrolytes by Frontal Analysis ContinuoU.S. Capillary Electrophoresis," Anal. Chem., 1997; 69:2945-2951.
Handbook of Chemistry and Physics, 88th Ed., 2008 (Viscosities of Liquids) Section 6, pp. 175-179.
Harada et al., "Formation of Polyion Complex Micelles in an Aqueous Milieu from a Pair of Oppositely-Charged Block Copolymers with Poly(ethylene glycol) Segments," Macromolecules, 1995; 28:5294-5299.

Hudecz et al., "Branched Polypeptides with a POLY-(L-Lysine) Backbone: Synthesis, Conformation, and Immunomodulation," *Polymeric Materials in Medication*, Plenum Press, New York, 1985; pp. 265-289.
Illum et al., "Effect of the Nonionic Surfactant Poloxamer 338 on the Fate and Deposition of Polystyrene Microspheres Following Intravenous Administration," *J. Pharm. Sci.*, 1983; 72(9):1086-89.
Jaworek et al., "Effects of Analogs of (pyro)Glu-His-Gly-OH on Food Consumption and Gastric Acid Secretion in Rats," *Life Science*, 1984; 34(26):2597-2603.
Kataoka, K. "Preparation of Novel Drug Carrier based on the Self-Association of Block Copolymer," Drug Delivery System, 1995; 10(5):363-370.
Kuroda et al., "Hierarchical Self-Assembly of Hydrophobically Modified Pullulan in Water: Gelation by Networks of Nanoparticles," *Langmuir*, 2002; 18:3780-86.
Maa et al., "Spray-Drying of Air-Liquid Interface Sensitive Recombinant Human Growth Hormone," *Journal of Pharmaceutical Sciences*, 1988; 87(2):152-159.
Mezo et al., "Synthesis and Conformation Studies of Poly(L-Lysine) Based Polypeptides with Ser and Glu/Leu in the Side Chains," *J. Controlled Release*, 2000; 63:81-95.
Oppenheim et al., "The Primary Structure and Functional Characterization of the Neutral Histidine-Rich Polypeptide from Human Parotid Secretion," *Journal of Biological Chemistry*, 1986; 261(3):1177-1182.
Regalado et al., "Viscoelastic Behavior of Semidilute Solutions of Multisticker Polymer Chains," Macromolecules, 1999; 32:8580-8588.
Shen, W.C., "Acid Sensitive Dissociative Between Poly(Lysine) and Histamine Modified Poly(Glutamate) as a Model for Drug Releasing From Carriers in Endosomes," 1990, Biochim. Biophys. Acts., 1034(1):122-124.
Tomida et al., *Convenient Synthesis of High Molecular Weight Poly(succinimide) by Acid-Catalysed Polycondensation of L-aspartic Acid, Polymer*, 1997: 38:4733-4736.
Tsutsumiuchi et al., "Synthesis of Polyoxazoline-(Glyco)peptide Block Copolymer Ring-opening Polymerization of (Sugar-Substituted) α Amino Acid N-Carboxyanhydrides with Polyoxazoline Macroinitiators," *Macromolecules*, 1997; 30:4013-4017.
Van Heeswijk et al., "The Synthesis and Characterization of Polypeptide-Adriamycin Conjugates and its Complexes with Adriamycin," *J. Controlled Release*, 1985; 1(4):301-315.
Volgler et al., *Helv. Chim. Acta*, 1964; 47:526-544.
Woodle et al., "Sterically Stabilized Liposomes," *Biochim. Biophys. Acta*, 1992; 1113(2):171-199.
Woodle, M.C., "Controlling Liposome Blood Clearance by Surface-Grafter Polymers," *Adv. Drug Deliv. Rev.*, 1998; 32(1-2):139-152.

\* cited by examiner

COLLOIDAL SUSPENSION OF NANOPARTICLES BASED ON AN AMPHIPHILIC COPOLYMER

This application is a U.S. National stage of International application PCT/FR02/01045, filed Mar. 26, 2002 which claims priority to French application 01/04512, filed Apr. 2, 2001.

The field of the present invention is that of Vectorization Nanoparticles (VP), which are useful for the administration of active principles (AP). These active principles are preferably medicinal products or nutrients for administration to an animal or human body via the oral or nasal, vaginal, ocular, subcutaneous, intravenous, intramuscular, intradermal, intraperitoneal, intracerebral, etc. route. In terms of chemical nature, APs that are most particularly concerned by the invention are hydrophilic, for example proteins, glycoproteins, peptides, polysaccharides, lipopolysaccharides or polynucleotides.

The present invention more specifically relates to colloidal suspensions of Vectorization Nanoparticles (VP), based on polyamino acid blocks and hydrophilic polymers of the type such as PolyAlkylene Glycol (PAG), preferably PolyEthylene Glycol (PEG).

The present invention is directed both toward VPs per se and toward AP vector systems, consisting of VPs charged with AP.

The present invention also relates to pulverulent solids comprising these VPs.

The invention also relates to processes for preparing said colloidal suspensions of particles charged with AP.

The combination of AP with VPs is especially directed toward modifying their duration of action and/or conveying them to the site of treatment and/or increasing the bioavailability of said APs. Numerous combination techniques have already been proposed. Such techniques are directed firstly toward allowing the AP to be transported to its site of therapeutic action, while at the same time protecting it against attack from the body (hydrolysis, enzymatic digestion, etc) and, secondly, toward controlling the release of the AP on its site of action, so as to maintain the amount available to the body at the desired level. The APs concerned by these changes in transportation and residence in the body are, for example, proteins, but may also be entirely different products, organic molecules of synthetic or natural origin. The review by M. J. Humphrey (Delivery system for peptide Drugs, edited by S. Davis and L. Illum, Plenum Press, N.Y. 1986) presents the problems regarding improving the bioavailability of APs and the advantage of systems for vectorization and controlled release.

Figure 1:
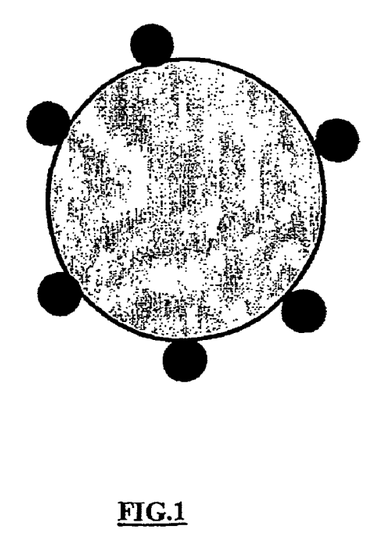
FIG. 1—Scheme of a vectorization particle of the type that adsorbs the AP.
Figure 2:
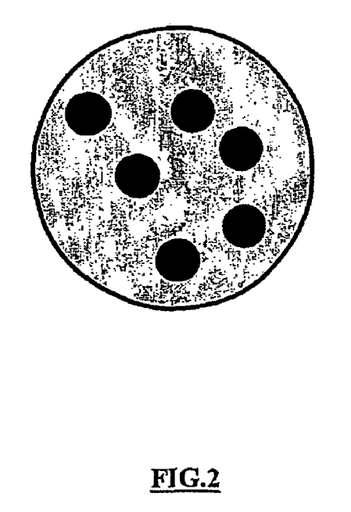
FIG. 2—Scheme of a vectorization particle of the type that encapsulates the AP.

In point of fact, two main types of system for vectorization and controlled release of AP are distinguished, which are characterized by the mode of combination of the AP with the VPs, namely:

combination by adsorption, illustrated by the attached FIG. 1, and combination by encapsulation (or by coating), illustrated by the attached FIG. 2.

Combination of the AP with the VPs by spontaneous adsorption is the system with which the present invention is concerned. Generally, spontaneous adsorption techniques are less aggressive with respect to APs than the techniques of combination by encapsulation, in which use is often made of solvents and/or surfactants, and also process steps (emulsification, evaporation, distillation) that are liable to denature the APs, and in particular APs of protein nature (preservation of the native secondary structure), which constitute the majority of the usual APs targeted. In the case of a combination by adsorption, the release takes place by desorption.

Beyond the modes of combination/release of the VPs with respect to the VPs, the constituent materials of the VPs must have particular working properties. Finally, the specifications that it is desired to obtain for the VPs are particularly stringent and especially comprise the following specifications.

1 A first specification desired for the VPs is:
   firstly, that the VPs combine easily with the APs to form VP-AP systems that allow a sustained release and sustained action of the AP in vivo (for example, a duration of action of at least 24 hours for an AP=insulin), and
   secondly, that these VPs (which may or may not be charged with AP) form aqueous suspensions that are stable (for example for at least several months), without the aid of organic solvent and/or surfactant; i.e. the VPs remain in suspension and do not flocculate.

2 The VPs should consist of a (co)polymer which is biocompatible, which can be eliminated (by excretion) and/or which is rapidly biodegradable into products that are not toxic for the body.

3 It is also desired for the VPs to have a size that is small enough to be able to undergo, in suspension in a liquid, a sterilizing filtration with a filter whose pore diameter is less than or equal to 0.2 µm.

4 It is desirable for the VPs and the VP-AP systems to be able to be obtained via a process that is not denaturing for the AP.

5 The VPs should, advantageously, allow the rate of release of the AP to be controlled.

6 Another important specification is that the VP-AP systems are able to constitute excellent injectable medicinal products. This improved capacity for administration by injection—e.g. intravenous or intramuscular—"injectability" is characterized by:
   (i) a reduced injected volume (for a given therapeutic dose),
   (ii) a low viscosity.
   These two properties are satisfied when the therapeutic dose of AP is combined with a minimum amount of VP. In other words, the VPs must have a high degree of charging with AP.

7. The cost intrinsic to the VPs in an injectable preparation must be low and, in this case also, the VPs should have a high degree of charging with AP. In the final analysis, the small size and a high degree of charging are major specifications desired for VPs.

8 It is also advantageous for the polymer constituting the VPs not to induce an immune response.

9 Finally, it is advantageous for the VPs to have a life time in the body which is not less than the release time desired for the AP.

The prior technical propositions (a) to (g), described below, attempted, in vain, to satisfy all these specifications.

(a) U.S. Pat. No. 5,286,495 relates to an encapsulation process by vaporization of proteins in an aqueous phase, using oppositely charged materials, i.e.: alginate (negatively charged) and polylysine (positively charged). This manufacturing process allows particles larger than 35 µm to be produced.

(b) Moreover, emulsion techniques are commonly used to prepare microparticles charged with AP. For example, patent applications WO 91/06286, WO 91/06287 and WO 89/08449 disclose such emulsion techniques in which use is made of organic solvents to dissolve polymers, for example of polylactic type. However, it was found that the solvents may be denaturing, especially for peptide or polypeptide APs.

(c) Biocompatible VPs known as proteinoids are also known, which were described as early as 1970 by X. Fox and K. Dose in "Molecular Evolution and the origin of Life", published by Marcel Dekker Inc. (1977). Thus, patent application WO 88/01213 proposes a system based on a mixture of synthetic polypeptides, the solubility of which depends on the pH. To obtain the matrix microparticles according to said invention, they dissolve the mixture of polypeptides and then, with a change in pH, they bring about the precipitation of proteinoid particles. When the precipitation takes place in the presence of an AP, this AP is encapsulated in the particle.

(d) Mention will also be made, as a reminder, of U.S. Pat. No. 4,351,337, which relates to a different field than that of the vectorization of AP that is intrinsic to the invention. Said patent discloses solid implants fixed and localized in quite specific places in the body. These implants are hollow tubes or capsules of microscopic size (160 μm and with a length equal to 2 000 μm), consisting of copolymers of copoly (amino acids)—e.g. poly(glutamic-leucine) or poly(benzyl glutamate-leucine)—obtained by copolymerization of amino acid N-carboxyanhydride (NCA) monomers. The inclusion of an AP takes places by means of a technique of evaporating solvent from a mixture of polymer and AP. U.S. Pat. No. 4,450,150 belongs to the same family as U.S. Pat. No. 4,351,337 studied above and has essentially the same subject. The constituent PAAs are poly(glutamic acid-ethyl glutamate)s.

(e) Patent application PCT/FR WO 97/02810 discloses a composition for the controlled release of active principles, including a plurality of lamellar particles of a biodegradable polymer, which is at least partly crystalline (lactic acid polymer) and of an AP adsorbed onto said particles. In this case, the release of the active principle takes place by desorption.

(f) Patent application PCT WO 96/29991 has as its subject matter polyamino acid particles that are useful for vectorizing APs such as insulin. These particles are between 10 and 500 nm in size.

The particles according to WO 96/29991 form spontaneously by placing PAA in contact with an aqueous solution. PAAs comprise a hydrophobic block formed by neutral and hydrophobic amino acid monomers OAA (polyLeu) and a hydrophilic block formed by ionizable and hydrophilic monomers IAA (polyGlu).

(g) EP 0 583 955 discloses polymer micelles capable of physically trapping hydrophobic APs. These micelles consist of block copolymers including a hydrophilic block consisting of polyethylene glycol (PEG) and a hydrophobic block consisting of a polyamino acid, for example: PEG/polyONAA (ONAA=hydrophobic neutral amino acid).

The ONAA may be: Leu, Val, Phe, Bz-O-Glu or Bz-O-Asp, this last amino acid being preferred. The hydrophobic AP active principles trapped in these PEG/polyONAA micelles are, for example: adriamycin, indomethacin, daunomycin, methotrexate, mitomycin.

In this patent application, the only examples presented are micelles based on PEG/polyGlu-O-Bz. Now, it is known that these Glu-O-Bz esters are not stable to hydrolysis in aqueous medium. In addition, the enzymatic hydrolysis of these products forms potentially toxic unnatural benzene derivatives. Moreover, nowhere in said document is it a matter of particles consisting of a PEG/polyONAA block copolymer, the core of which is formed by the hydrophobic neutral polyamino acid and comprising hydrophilic outer hair based on PEG, these particles being capable of combining with hydrophilic APs and of releasing them in vivo.

It is moreover known that PEGs are not biodegradable and are even capable of protecting VPs from enzymatic degradation, thus impairing the in vivo biodegradability of the VPs, which is one of the essential characteristics desired in the context of the present invention.

It thus emerges from the foregoing text that the prior technical propositions described above do not completely satisfy the specifications indicated above, and in particular specifications 1 (sustained duration of release and of in vivo action and stability in aqueous suspension of the VPs), 2 (biodegradability), 4 (non-denaturing production), 5 (controlled rate of release) and 8 (absence of immune response).

Given this state of affairs, one of the essential objectives is to be able to provide novel VPs (of the adsorption/desorption type) which spontaneously form, without the aid of surfactants or organic solvents, stable aqueous suspensions of VPs that are suitable for vectorizing APs (especially proteins such as insulin) and which above all make it possible to significantly increase the duration of release and of action in vivo of the AP, compared with the vectorization systems known in the prior art and presented above (a-g, see above).

Another essential objective of the present invention is to provide novel VPs as a colloidal aqueous suspension that is stable (especially to hydrolysis) or in pulverulent form and based on polyalkylene glycol (PAG)/poly(amino acids) (PAA) block copolymers, these novel VPs needing to optimally satisfy specifications 1 to 9 of the above-targeted list of specifications.

Another essential objective of the invention is to improve upon the particles disclosed in patent application EP 0 583 955.

Another essential objective of the invention is to provide a VP suspension which, although having an outer crown of PEG, is, nevertheless, readily biodegradable.

Another essential objective of the invention is to provide a novel VP suspension whose characteristics are fully controlled, especially in terms of the degree of charging with AP and in terms of control of the AP release kinetics.

Another essential objective of the invention is to provide stable medicinal VP suspensions that may be administered to man or animals, for example via the oral or parenteral route.

Another essential objective of the invention is to provide an aqueous colloidal suspension or a pulverulent solid comprising vectorization particles of active principles that satisfy the specifications targeted above and that consist of a presentation form that is appropriate and suitable for administration, for example an oral administration, to man or animals.

Another essential objective of the invention is to propose a process for preparing particles (dry or as a suspension in a liquid) of PAAs that are useful, especially, as vectors for active principles (especially proteins such as insulin), said process needing to be simpler to carry out, non-denaturing for the active principles and also needing to still allow fine control of the mean particle size of the particles obtained.

Another essential objective of the invention is the use of the abovementioned particles in aqueous suspension or in solid form for the preparation of medicinal products (e.g. vaccines), in particular for administration, especially oral, nasal, vaginal, ocular, subcutaneous, intravenous, intramuscular, intradermal, intraperitoneal or intracerebral administration, the hydrophilic active principles of these medicinal products possibly being, especially, proteins, glycoproteins, peptides, polysaccharides, lipopolysaccharides, oligonucleotides and polynucleotides.

Another objective of the present invention is to provide a medicinal product, of the type comprising a system with sustained release of active principles, which is easy and economical to produce and which is also biocompatible and capable of ensuring a very high level of bioavailability of the AP.

Another essential objective of the invention is to provide a vaccine vectorization system, which is not immunogenic intrinsically and in combination with one or more antigens.

These objectives (among others) are achieved by the present invention, which relates, firstly, to a colloidal suspension of nanoparticles that may be used especially for vectorizing active principle(s) (AP(s)), these particles being individualized supramolecular arrangements. The particular feature of this suspension is that said particles:

are based on at least one amphiphilic copolymer including:
  at least one block of hydrophilic polymer(s) of the polyalkylene glycol (PAG) type, preferably polyethylene glycol (PEG); and
  at least one linear amphiphilic copolyamino acid (PAA), containing α-peptide chains; and
are capable of combining in colloidal suspension in undissolved form, with at least one AP and of releasing said AP, especially in vivo, in a sustained and/or delayed manner.

One of the inventive grounds of these novel vectorization particles VPs, in stable colloidal aqueous suspension or in pulverulent solid form, relates to the novel selection of an amphiphilic PAG/PAA copolymer, for example a [hydrophilic polymer/hydrophilic polyamino acid/hydrophobic polyamino acid] block terpolymer, allowing the production of particles of nanometric size (10-500 nm), which form an aqueous colloidal suspension that is stable, both with respect to hydrolysis and with respect to flocculation, in the absence of surfactants and/or solvents, and which can bind to APs by adsorption and release these APs by desorption. In the case of the present invention, the adsorption takes place naturally and spontaneously when the colloidal particles and the AP are placed in contact in an aqueous medium. The adsorption depends on the nature of the support (VP) and the amount of support available to the AP.

One of the major advantages of the present invention is that it leads to a VP-AP system having a significantly increased duration of action in vivo (for example 10 hours when AP=insulin), compared with the known systems, and especially compared with the system described in patent application WO 96/29991 and comprising poly(Glu)/polyLeu VPs.

Moreover, the fact that the VPs consist partly of a hydrophilic polyamino acid offers the advantage of an easy possibility of degradation of the VPs by enzymatic hydrolysis, which facilitates their removal from the body.

Preferably, the amino acids of the amphiphilic copolyamino acid(s) (PAA(s)) of which the particles are composed are of at least two types:
  a first type comprising at least one hydrophilic amino acid (IAA);
  a second type comprising at least one hydrophobic amino acid (OAA).

In practice, the amphiphilic copolyamino acid(s) (PAA(s)) of which the particles are composed advantageously include(s) at least one block that is hydrophilic overall and at least one block that is hydrophobic overall.

In accordance with the invention, the structure of the amphiphilic copolymers and the nature of the IAA and OAA amino acids are chosen such that:
  the polymer chains become spontaneously structured in the form of small particles (VPs),
  the particles form a stable colloidal suspension in water and in physiological medium,
  the VPs bind with proteins or other APs in aqueous medium (in the absence of organic solvent and/or surfactant), via a spontaneous mechanism that is not denaturing for the AP,
  the VPs release the APs from the AP-VP combination complex under physiological conditions, and more specifically in vivo, with pharmacokinetic and pharmacodynamic profiles that are suitable for uses as medicament; the release kinetics depend on the nature of the PAG/PAA copolymer (=polyIAA/polyOAA) that is the precursor of the VPs.

Thus, by varying the particular block structure of the copolymer, the phenomena of combination and of release of the AP can be controlled kinetically and quantitatively.

The hydrophobic fraction polyOAA participates in the aggregation of the polymer chains, which is central to the formation of the VPs.

According to one noteworthy mode of the invention:
  the hydrophilic amino acid(s) (IAA) are selected from the group comprising:
    amino acids with one or more ionizable chain(s), which is (are) at least partially ionized, preferably Glu and/or Asp and salts thereof and/or Lys; which are natural and nonnatural
    and mixtures thereof;
  and the hydrophobic amino acid(s) (OAA) are selected from the group comprising:
    natural neutral amino acids, advantageously those of the sub-group: Leu, Ile, Val, Ala, Pro, Phe, and mixtures thereof;
    rare or synthetic neutral amino acids, advantageously those of the sub-group; norleucin, norvalin, and mixtures thereof;
    derivatives of polar amino acids, advantageously those of the sub-group: methyl glutamate, ethyl glutamate, benzyl aspartate, N-acetyllysine, and mixtures thereof; and
    mixtures thereof.

According to one preferred embodiment of the invention, the amphiphilic copolyamino acid(s) (PAA(s)) of which the constituent amphiphilic copolymer of the particles is composed has a "block" structure.

According to one variant, this or these amphiphilic copolyamino acid(s) (PAA(s)) may have a "random" structure, provided that it still comprises at least one block that is hydrophilic overall and at least one block that is hydrophobic overall, which gives it its amphiphilicity.

The preferred "block" amphiphilic PAA advantageously includes:
  at least one block that is hydrophilic overall, consisting essentially of IAA amino acids, and having an absolute length of greater than or equal to 5 IAA monomers, preferably greater than or equal to 200 IAA monomers and even more preferably between 10 and 50 IAA monomers, and
  at least one block that is hydrophobic overall, consisting essentially of OAA amino acids, with an absolute length of greater than or equal to 5 OAA monomers, preferably greater than or equal to 10 OAA monomers and more preferably between 10 and 50 OAA monomers.

As regards the hydrophilic PAG—preferably PEG—it is advantageously in the form of a block with an absolute length of greater than or equal to 5 monomers, preferably between 5 and 120 monomers and even more preferably between 5 and 50 monomers. It should be noted that the PAG (e.g. PEG) blocks may be homopolymers or copolymers, homopolymers being more particularly appreciated.

Even more preferably, it is to the Applicant's credit to have chosen, as constituent material of the VPs, a particular class of block terpolymer: hydrophilic polymer/hydrophilic polyamino acid/hydrophobic polyamino acid, which are amphiphilic and charged. This amphiphilicity makes it possible to obtain novel and surprising properties and especially those mentioned above. Thus, the VPs according to the invention form stable aqueous suspensions, in the absence of any surfactant and of any organic solvent and at physiological pH values. Furthermore, by virtue of the choice of the triblock structure, comprising a hydrophilic block based on amino acids between the PAG portion and the hydrophobic portion, the VPs are readily degradable in vivo via an enzymatic hydrolysis reaction. This is one of the key points of the terpolymer system according to the preferred embodiment of the invention.

In addition, the VP/AP combinations form spontaneously and above all allow a release and thus action in vivo over very long periods (for example 30 hours or more with a protein such as insulin). Thus, the action time of the AP in vivo is long enough to significantly increase the therapeutic cover and thereby improve the patient's comfort.

According to one concrete working example of the invention, the particles consist of chains of "linear triblock" amphiphilic copolymers PEG/IAA/OAA, preferably corresponding to the following formula:

$$R1-(OCH_2CH_2)m-R2-(CO-CHNR_4)n-(CO-CHNR_6)y-R7$$
$$\phantom{R1-(OCH_2CH_2)m-R2-(CO-CHNR_4)n-(CO-}|\phantom{CHNR_6)y-R7}$$
$$\phantom{R1-(OCH_2CH_2)m-R2-(CO-}R3\phantom{n-(CO-}R5$$

in which
R1=H, linear or branched $C_1$-$C_{20}$ alkyl (substituted or unsubstituted), aryl, preferably benzyl (substituted or unsubstituted);
R2=NH, CO—NH, CS—NH, R8-$(CH_2)_t$-R9 with R8 and R9 chosen independently from OCO, OCONH, NHCO, NHCONH, CONH, COO, NH, CO; t=1-6, [NHCH(R1)CO—]$_x$;
R3=identical or different radicals along the chain and chosen from the groups defining the ionizable hydrophilic amino acids (natural or synthetic derivatives), i.e. preferably, the groups $(CH2)_pC_6H_4OM$, $(CH_2)_pCO_2M$, $(CH2)_pN(H_cR1_d)_3X$ with $p \geq 1$, preferably=1 or 2; a and b are values between 0 and 3 and a+b=3; X preferably being a chloride, bromide, sulfate, nitrate, hydrogen phosphate, acetate or lactate ion;
R4=identical or different radicals along the chain, chosen from H and Me groups;
R5=identical or different radicals along the chain, chosen from the groups defining the hydrophobic amino acids (natural or synthetic derivatives), i.e. preferably the groups H, R1, $(CH_2)_qC_6H_5$, $(CH_2)_q C_6H_4OR1$, $(CH_2)_q OR1$, $(CH_2)_q CO_2R1$, $(CH_2)_qCON(R1)_2$, with $q \geq 1$, preferably=1 or 2;
R6=R4;
R7=H, R1CO with R1 as defined above, linear or branched $C_1$-$C_{20}$ alkyl (substituted or unsubstituted), aryl, preferably benzyl (substituted or unsubstituted), $C_1$-$C_6$ hydroxyalkyl, H, $-(CH_2)_wOH$, $-(CH_2)_w CO_2M$, $-(CH_2)_w(CHR1)_zOH$, $-(CH_2)_wNH_2$, $-(CH_2)_yC_6H_4OH$, $(CH2)yCO—N(R1)_2$; R10=H, Me, $(CH_2)_vOH$., with w, z and $v \geq 1$ and M=metal or cation, typically an alkali metal such as Na, Li or K, or $NH_4$, $R1_aNH_b$;
m>1; n>3.; $y \geq 0$; a+b=4.

In accordance with the invention, having a hydrophilic polyamino acid (polyIAA) block in the copolymer constituting the VPs is a particularly advantageous arrangement in that it improves the biodegradability of the VPs. This polyIAA block is preferably arranged between a hydrophilic polymer block and a hydrophobic polyamino acid (polyOAA) block.

The VP particles according to the invention have a mean size of between 10 and 500 nm and preferably between 10 and 200 nm. For the purposes of the invention, the terms "mean size" and "mean particle size" mean the mean hydrodynamic diameter.

One of the advantages of the invention is that of achieving very good control of the mean particle size of these species and their particle size distribution.

The control of the self-association of the polymer chains, and thus of the VP size, takes place via the polyamino acid composition, but also, for the same composition, via the choice of a block structure and the production process. In this manner, the particle size is extremely small, of the order of a few nanometers to a few tens of nanometers.

The suspension according to the invention is aqueous and stable.

The present invention is directed not only toward suspensions of naked particles, as defined above, but also suspensions of particles including at least one active principle AP.

These particles, which may or may not be combined with an AP, are advantageously in dispersed form in an aqueous liquid, but may also be in the form of a pulverulent solid, obtained from the PV suspension as defined above.

The invention thus concerns, besides an aqueous colloidal suspension of VPs, a pulverulent solid comprising VPs and obtained from the suspension according to the invention.

It should be noted that the nature of the distribution of the hydrophobic groups on the polymer chains may be controlled by means of the synthetic route selected. In this regard, there are many reaction schemes leading to the polymers selected as starting material for obtaining the VPs according to the invention.

In accordance with the invention, one particular mode for preparing the VPs and the VP suspension is selected.

Thus, another essential subject of the invention relates to the preparation of the selected particles (as described above), both in the form of a colloidal suspension and in the form of a pulverulent solid. The preparation process under consideration consists essentially:
insynthesizing PAG/polyIAA/polyOAA copolymers which are precursors of the VPs and in converting them into structured VP particles;
optionally, in purifying the particles thus produced;
optionally, in isolating these particles, preferably by concentration, lyophilization, filtration or drying.

More specifically, the process is, firstly, a process for preparing the abovementioned pulverulent solid formed from structured nanometric particles that may be used especially for the vectorization of active principle(s), these particles being individualized supramolecular arrangements:
based on at least one amphiphilic copolymer including:
at least one hydrophobic block of linear polyamino acid(s) (PAA), containing (α-peptide chains, the hydrophobic amino acids OAA of which this PAA block is made being identical to or different than each other;

at least one hydrophilic block of linear polyamino acid(s) (PAA), containing (α-peptide chains, the hydrophobic amino acids IAA of which this PAA block is made being identical to or different than each other; and at least one block of hydrophilic polymer(s) of the polyalkylene glycol (PAG) type, preferably polyethylene glycol (PEG);

which are capable of combining in colloidal suspension, in nondissolved form, with at least one AP and in releasing this AP, especially in vivo, in a sustained and/or delayed manner.

This process is characterized in that:
1) at least one PAG block comprising at least one alkylene glycol monomer is reacted with at least one hydrophilic PAA block comprising at least one hydrophilic amino acid IAA monomer and with at least one hydrophobic PAA block including at least one hydrophobic amino acid OAA monomer, this PAG block and these blocks each comprising at least one reactive function so as to obtain a PAG/polyIAA/polyOAA "block" amphiphilic copolymer;
2) the PAG/polyIAA/polyOAA block amphiphilic copolymer obtained in step 1 is transferred into a medium that is a nonsolvent for the hydrophobic fraction(s) of the amphiphilic copolymer—preferably into water—, which leads to the spontaneous formation of vectorization particles (VPs);
3) optionally, the reaction medium is dialyzed to purify the aqueous suspension of structured particles;
4) optionally, this suspension from step 3 is concentrated;
5) optionally, at least one active principle AP is combined with the particles from step 2, 3 or 4;
6) the liquid medium is removed to collect the pulverulent solid including the charged or uncharged particles.

For the purposes of the invention, the term "nonsolvent" means that the fractions of the amphiphilic copolymer under consideration have, for example, a solubility of less than 1 g/l at 25° C. in the nonsolvent medium under consideration.

At the end of step 2, the liquid medium does not form a uniform solution, but separates out into a dispersed phase (VP) and a phase that is depleted in "block" amphiphilic copolymer.

The reactive functions of the PAG block(s) and of the polyOAA and polyIAA blocks from step 1 may be amine or carboxylic acid functions. It may be envisaged to perform the polymerization leading to the PAG block(s) and/or to the polyIAA hydrophilic block(s) and/or to the polyOAA hydrophobic block(s) before, during or after the formation of the PAG-polyIAA and/or PAG-polyOAA and/or polyIAA-polyOAA linkage.

All these variants are within the capability of a person skilled in the art.

Preferably, in step 1:
1.1) a copolymerization of monomers formed by N-carboxyamino acid (NCA) anhydrides of at least two different types, firstly of NCA-pIAA ("pIAA" denoting an IAA precursor) and secondly NCA-OAAs, is performed, in the presence:
of at least one polar solvent preferably chosen from the group comprising: N-methylpyrrolidone (NMP), dimethylformamide (DMF), dimethyl sulfoxide (DMSO), dimethylacetamide (DMAc), pyrrolidone; NMP being more particularly preferred; and optionally of at least one cosolvent selected from aprotic solvents (preferably 1,4-dioxane) and/or proptic solvents (preferably pyrrolidone) and/or water and/or alcohols, methanol being particularly preferred;

the pIAA repeating units of the PAA precursor copolymer of the particles is converted into IAA repeating units, by performing a hydrolysis, preferably an acidic hydrolysis, for which an acidic aqueous phase is added to the organic medium described above;

1.2) at least one PAG polymer block of polyalkylene glycol (preferably of PEG or PPG) is used or prepared by polymerization of alkylene glycol monomers (preferably ethylene glycol or propylene glycol); this PAG block being functionalized (advantageously only at one of its ends) with a reactive group preferably chosen from the group comprising amines (in particular primary or secondary amines), alcohols or thiols, activated carboxylic acids (by prior reaction with dicyclohexylcarbodiimide, carbonyldiimidazole or any other reagent known to those skilled in the art);

1.3) the functionalized PAG from step 2 is added to the medium for polymerization of the hydrophilic polyIAA and hydrophobic polyOAA blocks, before, during or after the polymerization.

Step 1.1 of the process is inspired from the known techniques for polymerizing N-carboxy-α-amino acid (NCA) anhydrides, described, for example, in the article "Biopolymers, 15, 1869 (1976)" and in the book by H. R. Kricheldorf "α-amino acid-N-carboxy-anhydride and related heterocycles" Springer Verlag (1987).

According to one variant, during step 1.1, the poly(OAA)-poly(IAA) copolymer obtained is precipitated—preferably in water—and this precipitate is collected. This variant corresponds to a batchwise mode for preparing particles, in which the poly(OAA)-poly(IAA) copolymer is isolated in the form of a precipitate forming a stable intermediate product. This precipitate may, for example, be filtered, washed and dried.

Even more preferably, the NCA-pIAAs are NCAs of O-alkylated glutamic or aspartic acid, for example NCA-Glu-O-Me, NCA-Glu-O-Et or NCA-Glu-O-Bz (ME=methyl–Et=ethyl).

More generally, the preparation of the particles may take place, for example, by addition of a nonsolvent for the hydrophobic fraction to a solution of the amphiphilic copolymer dissolved in a solvent, advantageously after synthesis of the terpolymer. The addition of the solution of the terpolymer to a nonsolvent for the hydrophobic fraction constitutes one variant of this process. The operation preferably consists in reducing the solubility of the hydrophobic fraction so that it aggregates, doing so to form the VPs. A person skilled in the art is capable of finding other means for reducing the solubility of the hydrophobic fraction of the polymer, for example by modifying the temperature, the nature of the solvent(s) and of the nonsolvent, or by combining different techniques.

For example, during this preparation of, a colloidal suspension, the PAG-poly(IAA)-poly(OAA) amphiphilic copolymers from step 1 are placed in an aqueous medium in which at least some of the PAGs is soluble and at least some of the OAAs is insoluble. The PAG-polyIAA-polyOAA copolymers exist in the form of nanoparticles in this aqueous medium.

One alternative for preparing the VP suspension according to the invention consists in placing the pulverulent solid, as described above as a product and by the process for obtaining it, in contact with an aqueous medium, and in particular with water, that is a nonsolvent for the hydrophobic fraction of the amphiphilic copolymer.

Thus, the VPs may be obtained in water in the absence of any solvent or surfactant.

Preferably, the functionalized PAG block(s) is (are) introduced before and/or at the start of the polymerization, which preferably proceeds at a temperature of between 20 and 120° C. at normal atmospheric pressure.

Advantageously, the PAGs from step 1.2 are commercially available products (e.g. PEG), or else are obtained in a manner that is known per se by polymerization of ethylene oxide.

Other parameters, such as the polymer concentration, the temperature of the reaction mixture, the mode of addition of the hydrophilic polymer, the use of reduced pressure, the reaction time, etc. are adjusted according to the desired effects and are well known to those skilled in the art.

The description of the characteristics of the polymers, given above in the context of the presentation of the particles, may be transposed in its entirety in the present description relating to the process. Thus, in accordance with the process according to the invention, the nature and amount of the repeating amino acids, and also the operating conditions, may be selected so as to obtain different types of polymers having the abovementioned characteristics.

To perform the combination (step 3) of one or more APs with the particles, it is possible to perform several methods in accordance with the invention. Nonlimiting examples of these methods are listed below.

According to a first method, AP is combined with the particles by placing a liquid phase (aqueous or nonaqueous) containing the AP in contact with the colloidal suspension of particles.

According to a second method, the AP is combined with the particles by placing an AP in solid form in contact with the colloidal suspension of particles. The solid AP may be, for example, in the form of a lyophilizate, a precipitate, a powder or the like.

According to a third method, the pulverulent solid (PAA), as described above as a product and by its production characteristics, is placed in contact with a liquid phase (aqueous or nonaqueous) containing the AP.

According to a fourth method, the pulverulent solid, as described above as a product and by its production characteristics, is placed in contact with the AP in solid form. This mixture of solids is then dispersed in a liquid phase, preferably an aqueous solution.

In all these methods, the AP used may be in pure or preformulated form.

The preparation of the VPs is advantageously followed by a purification step, involving techniques known to those skilled in the art. After this optional purification step, a colloidal suspension of VP is obtained, which may be used directly, or which it may be envisaged to isolate or collect by any suitable physical means known per se, for instance: by filtration, by concentration, by ultrafiltration, by density-gradient separation, by centrifugation, by precipitation, optionally by adding a salt, or by lyophilization.

In accordance with the optional step 5, the impurities (salts) and the solvent are removed by any suitable physical separation treatment, for example by diafiltration (dialysis) (step 4), filtration, pH modification, chromatography or distillation. Such methods make it possible to remove the unwanted salts or solvents.

To concentrate (step 6) or to separate (step 7) the structured particles obtained, from their liquid suspension medium, the aqueous phase is optionally removed, for example by distillation, by drying (e.g. in an oven), by lyophilization or any other suitable physical means: ultrafiltration, centrifugation. After this step 7, a pulverulent white solid is recovered.

Given the nanometric size of the particles, the suspension may be filtered through sterilization filters, which makes it possible to obtain sterile injectable medicinal liquids, readily and cheaply. Being able, by virtue of the invention, to control the size of the particles and to achieve hydrodynamic diameter (Dh) values of between 25 and 100 nm is an importance advantage.

The present invention is also directed toward novel intermediate products of the process described above, characterized in that they consist of PAG-polyIAA-polyOAA copolymers that are particle precursors.

According to another of its aspects, the invention relates to a suspension and/or a pulverulent solid, as defined above and/or as obtained by the process presented above, this suspension and this solid including at least one active principle preferably chosen from:

vaccines, taken alone or combined with at least one antigen;

proteins and/or peptides, among which the ones most preferably selected are: hemoglobins, cytochromes, albumins, interferons, antigens, antibodies, erythropoietin, insulin, growth hormones, factors VIII and IX, interleukins or mixtures thereof, and hematopoiesis-stimulating factors;

polysaccharides, heparin being more particularly selected;

nucleic acids, and preferably RNA and/or DNA oligonucleotides;

nonpeptide-protein molecules belonging to various anticancer chemotherapy classes, and in particular anthracyclines and taxoids;

and mixtures thereof.

Finally, the invention relates to a pharmaceutical, nutritional, plant-protection or cosmetic speciality product, characterized in that it includes a suspension and/or a pulverulent solid charged with AP and as defined above.

According to another of its subjects, the invention is also directed toward the use of these VPs (in suspension or in solid form) charged with AP, for the manufacture of medicinal products of the type such as systems with controlled release of AP.

They may be, for example, medicinal products that may preferably be administered via the oral, nasal, vaginal, ocular, subcutaneous, intravenous, intramuscular, intradermal, intraperitoneal or intracerebral route The cosmetic applications that may be envisaged are, for example, compositions comprising an AP combined with the VPs according to the invention, which may be applied transdermally.

The examples that follow and that relate to the hydrophilic AP formed by insulin will allow the invention to be understood more clearly in its various product/process/application aspects. These examples illustrate the preparation of polyamino acid particles optionally charged with AP, and similarly they have the structure characteristics and the properties of these particles.

EXAMPLES

Example 1

Preparation of poly(leucine)12-block-poly(glutamate)35-(polyethylene glycol)113

The techniques used for the polymerization of the NCAs into polymers of block or random structure are known to those skilled in the art and are detailed in the book by H. R. Kricheldorf "α-Amino Acid-N-Carboxy Anhydrides and Related Heterocycles", Springer Verlag (1987). The following synthesis specifies the synthesis of one of them.

4.96 g of aminoethyl-PEG (molar mass 5000; Degree of Polymerization (DP) 113) are dissolved in 120 ml of NMP at 40° C. 1.4 ml of MeOH are added thereto, followed by addition of 6.4 g of NCA-GluOMe in a single portion. After half an hour, 1.8 g of NCA-Leu are added and the reaction is continued for 2 hours. Next, dilute hydrochloric acid is added to the reaction medium and the resulting mixture is heated at 80° C. for 24 hours. At 50° C., the medium is neutralized with 6 N sodium hydroxide. This intermediate is dialyzed against water to remove the small soluble residues (solvent, salts). The purified solution is freeze-dried to give a white powder. 80% yield.

Example 2

Preparation of poly(leucine)12-block-poly(glutamate)18-(polyethylene glycol)17

2.01 g of aminoethyl-PEG (molar mass 750; DP 17) are dissolved in 45 ml of NMP at 40° C. 1.5 ml of MeOH are added thereto, followed by addition of 9 g of NCA-GluOMe in a single portion. After half an hour, 5 g of NCA-Leu are added and the reaction is continued for 2 hours. Next, dilute hydrochloric acid is added to the reaction medium and the resulting mixture is heated at 80° C. for 24 hours. At 50° C., the medium is neutralized with 6 N sodium hydroxide. This intermediate is dialyzed against water to remove the small soluble residues (solvent, salts). The purified solution is freeze-dried to give a white powder. 80% yield.

Example 3

Demonstration of the Nanoparticles by Light Scattering (LS) and by Transmission Electron Microscopy (TEM)

10 mg of the copolymer obtained in example 1 or 2 are suspended in 10 ml of water or an aqueous salt solution. This solution is then introduced into a Coulter granulometer (or laser diffractometer). The results of the particle size analysis for the various products tested are presented in table 1 below.

TABLE 1

| VP size measurements | | |
| --- | --- | --- |
| Example | Polymer | Size (nm) |
| 1 | $PEG_{113}$-3 $(GLU)_{35}$-$(LEU)_{12}$ | 80 |
| 2 | $PEG_{17}$-$(GLU)_{18}$-$(LEU)_{12}$ | 41 |

Figure 4:
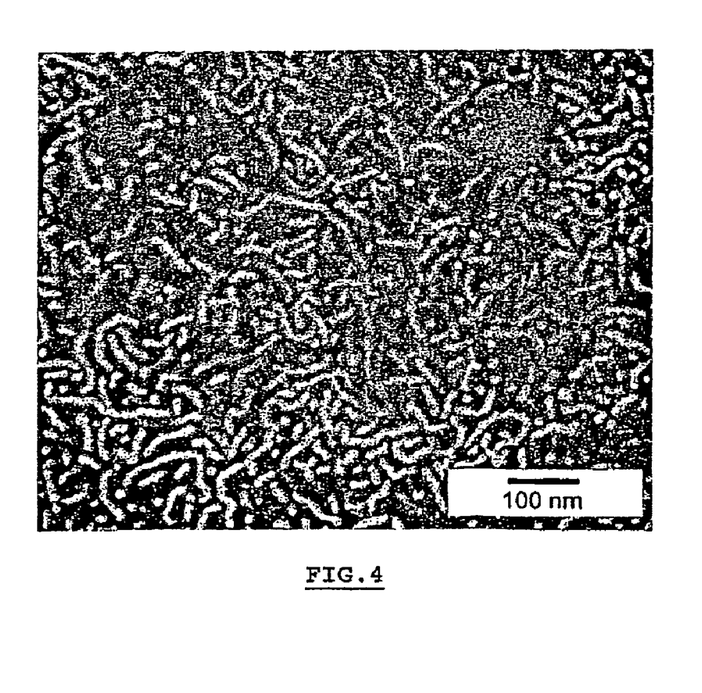
FIG. 4—Photograph of VPs (example 2) by transmission electron microscope.

The vectorization particles VP prepared in the present example by suspending the amphiphilic copolymer of example 2 in water are also photographed with a transmission electron microscope (FIG. 4 attached).

Example 4

Test of Combination of the Nanoparticles with a Protein (Insulin)

Starting with isotonic phosphate buffer solution of pH 7.4, a human insulin solution with a titer of 1.4 mg/ml, corresponding to 40 IU/ml, is prepared. 10 mg of the amphiphilic copolymer according to example 1 or 2 are dispersed in 1 ml of this insulin solution. After incubation for 15 hours at room temperature, the insulin combined with the vectorization particles VP and the free insulin are separated by centrifugation (60 000×g, 1 hour) and ultrafiltration (filtration threshold 300 000 D). The free insulin recovered in the filtrate is assayed by High Performance Liquid Chromatography or by ELISA and the amount of combined insulin is deduced therefrom by difference.

Table 2 below collates the results of the measurements of the degrees of combination performed on different VPs. The degree of combination expresses the percentage of combined insulin relative to the insulin used in a preparation with a titer of 1.4 mg/ml of insulin and 10 mg/ml of VP. This value is converted into a degree of charge, which expresses the maximum amount of insulin in mg that can be combined with 100 mg of VP.

TABLE 2

| Measurements of the degree of combination with insulin for a 0.14 mg INSULIN/mg VP mixture | | |
| --- | --- | --- |
| Example | Polymer | Max. degree of charge mg/100 mg VP |
| 1 | $PEG_{113}$-$(GLU)_{35}$-$(LEU)_{12}$ | 10 |
| 2 | $PEG_{17}$-9$(GLU)_{18}$-$(LEU)_{12}$ | 19 |

Example 5

Pharmacokinetics and Pharmacodynamics of VPs Charged with Insulin in the Case of Healthy Fasted Dogs The suspension of VP charged with insulin, prepared in example 4, was injected into two dogs rendered diabetic by total pancreatectomy, and fasted from the evening of the previous day. Thoracic subcutaneous administration of the preparation at 11 a.m. was performed at a dosage of 0.5 IU/kg of insulin per kg of live weight of the animal. The volume administered is between 0.18 and 0.24 ml. At time −4, −2, 0, 1, 2, 4, 6, 8, 12, 16, 20, 24, 28, 32, 36, 40, 44 and 48 hours, 1 ml of blood is collected by jugular puncture under vacuum onto a tube of sodium heparinate. 30 μl of whole blood are used extemporaneously to measure the glycemia. The tube is then centrifuged and decanted, and the plasma is stored at −20° C. for assay of the insulin. The results given in FIG. 3 below show a large hypoglycemiant effect (on both animals) which continues at least up to 24 hours after the injection.

TABLE 3

Measurements of the insulin action time (hypoglycemiant effect) in the presence of VPs according to the invention

Figure 3:
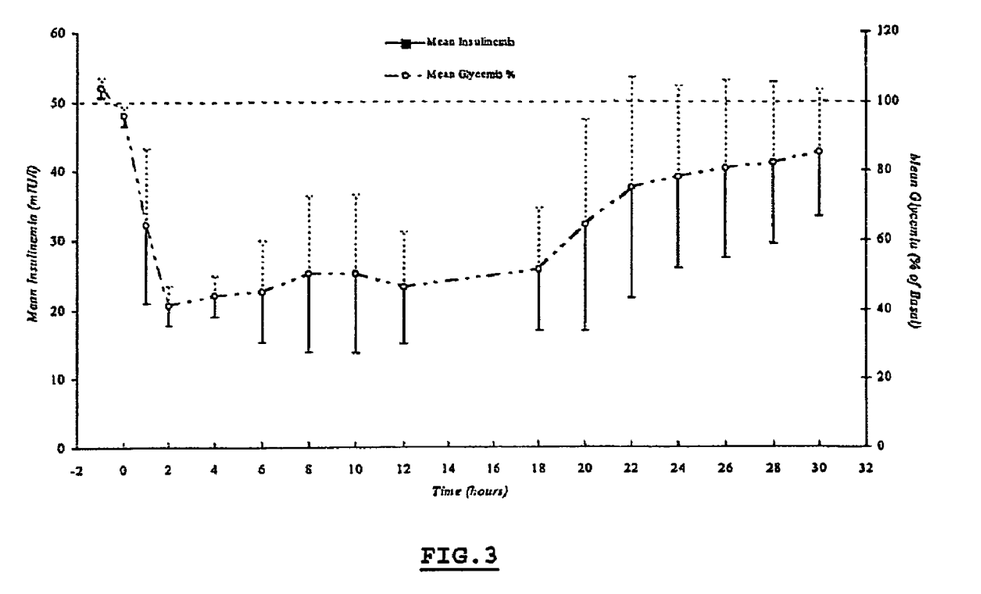
FIG. 3—Change in glycemia G (mean as % basal) after injection of a formulation of VP (example 5) charged with insulin to a proportion of 0.6 IU/kg, as a function of time t (in hours).

| Example | Polymer | Time for the glycemia to return to the basal level (in hours) | |
|---|---|---|---|
| | Soluble insulin (without VP) | 1 | |
| 1 | $PEG_{113}$-$(GLU)_{35}$-$(LEU)_{12}$ | — | |
| 2 | $PEG_{17}$-$(GLU)_{18}$-$(LEU)_{12}$ | >30 | FIG. 3 |

This example demonstrates the non-denaturation of insulin in the presence of VPs according to the invention.

Furthermore, this example makes it possible to demonstrate the increase to more than 30 hours of the duration of action of insulin compared with unformulated insulin, and thus the utility of the VPs as a delay system for the controlled release of insulin. It also shows how it is possible to control the action time by means of an appropriate choice of the hydrophobic group.

Comparative Example 6

Preparation of the poly(leucine)40-block-(polyethylene glycol)113 Polymer

Synthesis of poly$(Leu)_{40}$-PEG: 10 g of NCA-Leu are dissolved in 150 ml of NMP at 60° C. 5 ml of a solution of 2 g of aminoethyl-PEG (Mw 5000) in 50 ml of NMP are added to the monomer in a single portion. After 2 hours, the reaction medium is poured into 1 L of water. The precipitate formed is filtered off, washed and dried. Yield>95%.

The precipitate is dissolved in 100 ml of trifluoroacetic acid, followed by addition thereto of 40 ml of water over a period of one hour. The suspension is then neutralized with sodium hydroxide, dialyzed against water to remove the salts thus formed, and freeze-dried to obtain a solid product.

Comparative Example 7

Pharmacokinetics and Pharmacodynamics of VPs Combined with Insulin, in Healthy Fasted Dogs The VPs of example 6 are formulated and then injected into animals according to the protocol given in example 5. The results given in FIG. 5 below show a hypogylcemiant effect (on both animals), which continues up to 20 hours after the injection.

Example 8

Formulation Stability Comparison

The VPs of example 6, PEG-$Leu_{25}$ are formulated according to example 7. After standing for one month at +4° C., the formulation forms a deposit of precipitate, which does not dissolve at 35° C., showing the instability of this VP formulation.

The VPs of example 1 (poly(leucine)12-block-poly (glutamate)35-poly(ethylene glycol-)113 are formulated according to example 7. After standing for one month at +4° C., the formulation remains transparent and does not form a deposit of precipitate, showing the stability of this VP formulation and thus the advantage of a PEG-pplyIAA-polyOAA triblock copolymer over the PEG-polyOAA diblock copolymer.

Comparative Example 9

Preparation of the poly(leucine)12-block-(sodium glutamate)35 Polymer and its Pharmacodynamic Analysis The polymer is prepared according to example 1 with the following modification, the aminoethyl-PEG of Mw=5000 and of DP=113 is replaced with an equivalent molar amount of aqueous ammonia. The VPs are isolated, formulated and injected according to the above examples (examples 2 and 5) at a rate of 50 mg of VP per 100 IU of insulin. The results given in FIG. 6 below show a hypoglycemiant effect (on both animals) which continues up to 20 hours after the injection.

Comments:

TABLE 4 comparison of the in vivo action times of plain insulin, of insulin combined with vectorization systems of the prior art (comparative examples 6 and 8) and of insulin combined with the vectorization particles according to the invention (example 2)

Figure 5:
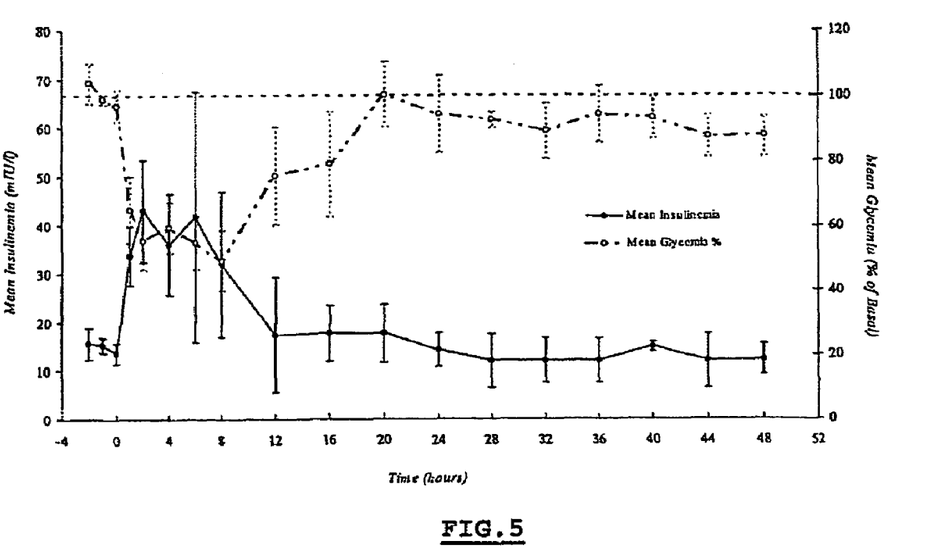
FIG. 5—Change in the glycemia (mean as % basal) and in the mean insulinemia I (in MU/l) in dogs, as a function of time t (in hours), after injection of a VP formulation (example 6) charged with insulin to a proportion of 0.6 IU/kg FIG. 6—Change in the glycemia G (mean as basal %) and in the mean insulinemia I (in MU/l) in dogs, as a function of time t (in hours) after injection of a VP formulation (example 9) charged with insulin to a proportion of 0.6 IU/kg.
Figure 6:
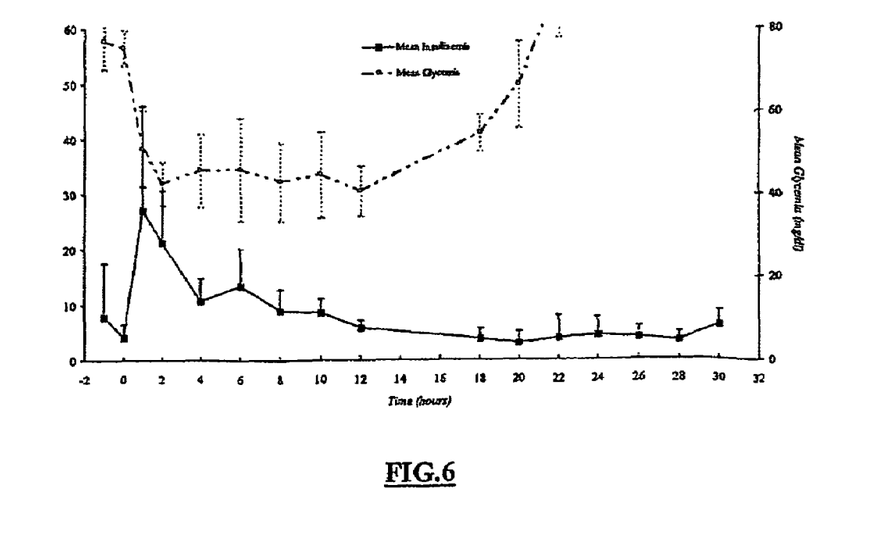

| Example | Polymer | Time for the glycemia to return to the basal level (h) | |
|---|---|---|---|
| | Soluble insulin (without VP) | 1 | |
| 2 | $PEG_{17}$-$(GLU)_{18}$-$(LEU)_{12}$ | >30 | FIG. 3 |
| 6 comp | $PEG_{113}$-$LEU_{40}$ | 20 | FIG. 5 |
| 8 comp | $(GLU)_{35}$-$(LEU)_{12}$ | 20 | FIG. 6 |

It emerges from this table that the system according to the invention (example 2) has an in vivo action time that is markedly longer (+ than 30 hours versus 20 hours) than that of the systems of the prior art (WO 96/29991): examples 6 and 8.

The invention claimed is:

1. A colloidal suspension comprising submicronic particles, wherein the particles:
   comprise at least one amphiphilic copolymer comprising at least one block of hydrophilic polyalkylene glycol polymer and at least one linear, α-peptide-linked copolyamino acid comprising at least one block of hydrophilic amino acid monomers with one or more ionizable chains which are at least partially ionized and having an absolute length of greater than or equal to 5 IAA monomers and a block of hydrophobic amino acid monomers having an absolute length of greater than or equal to 5 OAA monomers, wherein the copolyamino acid has a block structure;
   are individualized supramolecular arrangements;
   are in a nondissolved state;

will spontaneously associate with at least one active principle by adsorption, and without the aid of organic solvents or surfactants, when at least one active principle is added to the colloidal suspension; and release of the at least one active principle is in either or both a sustained manner or a delayed manner.

2. The colloidal suspension of claim 1, wherein the at least one block of hydrophilic polyalkylene glycol polymer has an absolute length of greater than or equal to 5 monomers.

3. The colloidal suspension of claim 1, wherein the particles comprise at least one amphiphilic copolymer comprising a linear triblock of polyethylene glycol, at least one block of hydrophilic amino acid monomers with one or more ionizable chains and having an absolute length of greater than or equal to 5 IAA monomers, and a block of hydrophobic amino acid monomers having an absolute length of greater than or equal to 5 OAA monomers.

4. The colloidal suspension of claim 3, wherein the at least one amphiphilic copolymer comprises a linear triblock of polyethylene glycol, glutamate in the at least one block of hydrophilic amino acid monomers, and leucine as the hydrophobic amino acid monomer.

5. The colloidal suspension of claim 1, wherein the particles have a mean size of between 10 and 500 nm.

6. The colloidal suspension of claim 1, wherein the suspension is aqueous and stable.

7. The colloidal suspension of claim 1, wherein the suspension further comprises at least one active principle.

8. The colloidal suspension of claim 7, wherein the at least one active principle is a vaccine, a protein, a peptide, a polysaccharide, a nucleic acid, an anticancer chemotherapeutic, or a mixture thereof.

9. The colloidal suspension of claim 7, wherein the at least one active principle is a hemoglobin, a cytochrome, an albumin, an interferon, an antigen, an antibody, erythropoietin, insulin, a growth hormone, factor VIII, factor IX, an interleukin, a hematopoiesis-stimulating factor, heparin, RNA, a DNA, an anthracycline, a taxoid, or a mixture thereof.

10. A process for preparing the colloidal suspension of claim 7, comprising contacting the colloidal suspension of claim 1 with a liquid phase containing the at least one active principle, to thereby obtain a colloidal suspension of particles further comprising at least one active principle.

11. A process for preparing the colloidal suspension of claim 7, comprising contacting the colloidal suspension of claim 1 with a solid phase containing the at least one active principle, to thereby obtain a colloidal suspension of particles further comprising the at least one active principle.

12. A pulverulent solid comprising submicronic particles, wherein the pulverulent solid is produced by removing liquid from the colloidal suspension of claim 1, to thereby produce a pulverulent solid comprising submicronic particles.

* * * * *